United States Patent
Makino

(10) Patent No.: US 7,301,143 B2
(45) Date of Patent: Nov. 27, 2007

(54) METHOD AND SYSTEM FOR READING OPTICAL INFORMATION

(75) Inventor: Kazuhiro Makino, Kanagawa-ken (JP)

(73) Assignee: Fujifilm Corporation, Tokyo (JP)

( * ) Notice: Subject to any disclaimer, the term of this patent is extended or adjusted under 35 U.S.C. 154(b) by 93 days.

(21) Appl. No.: 11/094,212

(22) Filed: Mar. 31, 2005

(65) Prior Publication Data

US 2005/0219534 A1    Oct. 6, 2005

(30) Foreign Application Priority Data

Mar. 31, 2004    (JP)    ............... 2004-103598

(51) Int. Cl.
*H04N 1/04*    (2006.01)
(52) U.S. Cl. .................. 250/234; 358/525
(58) Field of Classification Search ............... 250/234, 250/458.2, 458.1; 358/497, 525; 356/417
See application file for complete search history.

(56) References Cited

U.S. PATENT DOCUMENTS

| | | | |
|---|---|---|---|
| 5,469,216 A | | 11/1995 | Takahashi et al. |
| 6,252,236 B1 * | | 6/2001 | Trulson et al. ........... 250/458.1 |
| 6,496,608 B1 * | | 12/2002 | Chui ......................... 382/300 |
| 6,567,192 B1 * | | 5/2003 | Toyomura et al. ........... 358/497 |
| 6,762,840 B1 * | | 7/2004 | Kimura ...................... 356/417 |
| 7,088,392 B2 * | | 8/2006 | Kakarala et al. ............ 348/272 |
| 7,115,848 B1 * | | 10/2006 | Zinter et al. ............. 250/201.3 |

FOREIGN PATENT DOCUMENTS

| | | |
|---|---|---|
| JP | 7162848 | 6/1995 |
| JP | 2000196818 | 7/2000 |
| JP | 2001326912 | 11/2001 |
| JP | 2003-29361 A | 1/2003 |
| JP | 2003174543 | 6/2003 |

* cited by examiner

*Primary Examiner*—John R. Lee
(74) *Attorney, Agent, or Firm*—Sughrue Mion Pllc.

(57) ABSTRACT

Checkered light-intensity pixel data is acquired by shifting the sampling timing of even-numbered horizontal scan lines from the sampling timing of odd-numbered horizontal scan lines by one-half of a sampling cycle. Each of the interpolated light-intensity pixel data for the checkered light-intensity pixel data is obtained by calculating the average value of four checkered light-intensity pixel data on up-and-down and right-and-left sides of each of the interpolated light-intensity pixel data. Light-intensity image data is generated by interpolating the interpolated light-intensity pixel data into the checkered light-intensity pixel data. The data interval in the light-intensity image data becomes twice the pixel density of the checkered light-intensity pixel data.

15 Claims, 3 Drawing Sheets

METHOD AND SYSTEM FOR READING OPTICAL INFORMATION

BACKGROUND OF THE INVENTION

1. Field of the Invention

This invention relates generally to methods and systems for reading optical information, and more particularly to optical information reading methods and systems for detecting an intensity of light emitted from a scanned body with light-intensity detection means by horizontal and vertical scanning, and acquiring light-intensity image data.

2. Description of the Related Art

A conventional system for reading optical information is shown in U.S. Pat. No. 6,762,840 by way of example. This system has light-intensity detection means for detecting a light intensity by receiving light that is emitted from a scanned body, and scans the entire surface of the scanned body by repeatedly moving the light-intensity detection means relatively with respect to the scanned body in a horizontal scanning direction and in a vertical scanning direction nearly perpendicular to the horizontal scanning direction, and acquires light-intensity image data of the light emitted from the scanned body, based on an output signal from the light-intensity detection means.

For example, in the biochemistry and molecular biology fields, the aforementioned optical information read system is used in fluorescence detection systems that use a fluorescence labeling body as a labeling substance, and in chemical luminescence detection systems that use a chemical luminescence labeling body as a labeling substance.

Fluorescence detection systems can evaluate gene arrangement, gene expression levels, the path and state of the metabolism, absorption, and excretion of dosed substances in experimental mice, the separation and identification, or molecular weight and characteristics of protein, by irradiating excitation light to a gel sample in which inspection substances labeled with a fluorescence labeling body are distributed, and photoelectrically reading out fluorescence that is emitted from the gel sample when struck by the excitation light.

For instance, the molecular weight of a DNA fragment can be evaluated by electrophoresis in which charged living cells in suspension or charged biological compounds (protein, etc.) in a solution are moved to a positive or negative pole under the influence of an electric field. That is, after a fluorescence labeling body is added in a solution containing a plurality of DNA fragments, the DNA fragments are electrophoresed on a gel support; or a plurality of DNA fragments are electrophoresed on a gel support that contains a fluorescence labeling body; or after a plurality of DNA fragments are electrophoresed on a gel support, this gel support is immersed in a solution containing a fluorescence labeling body. In this manner, a gel support is obtained in which DNA fragments labeled with fluorescence are distributed. By irradiating excitation light, which excites a fluorescence labeling body employed as a labeling substance, to the gel support, the light intensity of the fluorescent light emitted from the gel support is photoelectrically read out. In this manner, light-intensity image data representing the distribution of DNA fragments labeled with fluorescence are acquired. Based on the obtained light-intensity image data, a visible image is displayed on a display unit such as a CRT display unit, whereby the molecular weight of the DNA fragment is evaluated.

The scanned body can employ a membrane or a glass slide in which inspection substances labeled with a fluorescence labeling body are distributed, in addition to the aforementioned gel support.

In chemical luminescence detection systems, a chemical luminescent substrate is brought into contact with a sample in which inspection substances labeled with a chemical luminescence labeling body are distributed, and the light intensity of the chemical luminescence emitted from the chemical luminescent substrate is photoelectrically read out. In this manner, light-intensity image data representing the distribution of inspection substances labeled with the chemical luminescence labeling body can be acquired.

As one example of a scanned body from which optical information is read out by optical information read systems, there is known a storable phosphor (stimulable phosphor) in which if radiation (X-rays, $\alpha$-rays, $\beta$-rays, $\gamma$-rays, electron rays, ultraviolet rays, etc.) is irradiated, part of the radiation energy is stored and thereafter, if excitation light is irradiated, photostimulated luminescence (PSL) is emitted according to the stored energy. If radiation, transmitted through a subject such as a human body, is irradiated onto a storable phosphor sheet, the radiation image information carried by the radiation can be stored in the storable phosphor sheet. By scanning the storable phosphor sheet horizontally and vertically with excitation light such as a laser beam, photostimulated luminescence is emitted according to the stored radiation image information. By photoelectrically reading out the light intensity of the photostimulated luminescence, light-intensity pixel data is acquired for each pixel of the storable phosphor sheet. Based on the light-intensity pixel data, a sheet quantity of light-intensity image data is generated (e.g., see Japanese Unexamined Patent Publication No. 2003-029361). Thereafter, the generated light-intensity image data undergoes image processing, such as a gradation process, a frequency process, etc., suitable for observation and inspection. The processed light-intensity image data is displayed as a visible image on a display unit, such as a CRT display unit, and is used for diagnosis.

In the system disclosed in the aforementioned Publication No. 2003-029361, analog signals are obtained by reading out photostimulated luminescence with a photomultiplier tube (PMT) when reading out image information. By sampling and quantizing analog signals at predetermined intervals, the light-intensity pixel data of each pixel is acquired in a predetermined pixel density.

Visible images to be displayed are used to observe the fine structures of a scanned body, so it is desirable that visible images be reproduced in higher resolution. To meet this demand, it is desirable to acquire light-intensity image data at a high pixel density from a scanned body. For that reason, the pixel density can be enhanced by shortening the cycle during which signals output from the PMT are sampled. However, there are cases where a sampling frequency is set high to the degree that the entire sampling cycle is judged by the time of processing signals obtained. In such a case, unless the above-described processing time is shortened, it is difficult to shorten the sampling cycle. In addition, the use of a system with a high signal processing speed can be the cause of an increase in cost.

SUMMARY OF THE INVENTION

The present invention has been made in view of the above-described circumstances. Accordingly, it is the primary object of the present invention to provide an optical information read method and an optical information read system that are capable of practically enhancing the resolution of light-intensity image data without increasing the pixel density of light-intensity pixel data acquired from a scanned body.

An optical information read method of the present invention is a method of scanning the entire surface of a scanned body by repeatedly moving light-intensity detection means, which detects a light intensity by receiving light that is emitted from the scanned body, relatively with respect to the scanned body in a horizontal scanning direction and in a vertical scanning direction nearly perpendicular to the horizontal scanning direction, and acquiring light-intensity image data of the light emitted from the scanned body, based on an output signal from the light-intensity detection means. The optical information read method further comprises the step of acquiring checkered light-intensity pixel data from the scanned body, calculating interpolated light-intensity pixel data from the light-intensity pixel data arranged around the interpolated light-intensity pixel data, and generating the light-intensity image data based on the light-intensity pixel data and the interpolated light-intensity pixel data.

An optical information read system of the present invention is a system which comprises light-intensity detection means for detecting a light intensity by receiving light that is emitted from a scanned body, and which scans the entire surface of the scanned body by repeatedly moving the light-intensity detection means relatively with respect to the scanned body in a horizontal scanning direction and in a vertical scanning direction nearly perpendicular to the horizontal scanning direction and acquires light-intensity image data of the light emitted from the scanned body, based on an output signal from the light-intensity detection means. The optical information read system further comprises light-intensity image data generation means for acquiring checkered light-intensity pixel data from the scanned body, calculating interpolated light-intensity pixel data from the light-intensity pixel data arranged around the interpolated light-intensity pixel data, and generating the light-intensity image data, based on the light-intensity pixel data and the interpolated light-intensity pixel data.

The expression "moving the light-intensity detection means relatively with respect to the scanned body" includes the movement of an optical positional relationship in addition to the movement of a spatial positional relationship.

In the optical information read system of the present invention, the aforementioned light-intensity image data generation means may acquire the light-intensity pixel data by quantizing the output signal of the light-intensity detection means at predetermined sampling cycles. In this case, the timing at which even-numbered horizontal scan lines are sampled may be shifted from the timing at which odd-numbered horizontal scan lines are sampled, by one-half of the sampling cycle.

The sampling interval in the horizontal scanning direction may be twice the spacing in the vertical scanning direction between the scan lines.

The light emitted from the aforementioned scanned body may be light that is emitted from the scanned body when scanned with excitation light.

According to the optical information read method and system of the present invention, checkered light-intensity pixel data from the scanned body is acquired. Then, interpolated light-intensity pixel data is calculated from the light-intensity pixel data arranged around the interpolated light-intensity pixel data, and the light-intensity image data is generated based on the light-intensity pixel data and the interpolated light-intensity pixel data. Therefore, the data spacing in the light-intensity image data can be shortened without increasing the pixel density of the light-intensity pixel data acquired from the scanned body. That is, resolution can be practically enhanced.

According to the optical information read method and system of the present invention, the light-intensity image data generation means acquires the light-intensity pixel data by quantizing the output signal of the light-intensity detection means at predetermined sampling cycles, and the timing at which even-numbered horizontal scan lines are sampled is shifted from the timing at which odd-numbered horizontal scan lines are sampled, by one-half of the sampling cycle. In this case, checkered light-intensity pixel data can be readily acquired by only shifting the sampling timing of even-numbered horizontal scan lines from the sampling timing of odd-numbered horizontal scan lines.

In the case where the sampling interval in the horizontal scanning direction is twice the spacing in the vertical scanning direction between the scan lines, the data interval in the horizontal scanning direction becomes equal to the data interval in the vertical scanning direction by interpolating the interpolated light-intensity pixel data in the light-intensity pixel data, and visibility when the interpolated light-intensity image data is displayed is enhanced.

BRIEF DESCRIPTION OF THE DRAWINGS

The present invention will be described in further detail with reference to the accompanying drawings wherein.

DESCRIPTION OF THE PREFERRED EMBODIMENT

Figure 1:
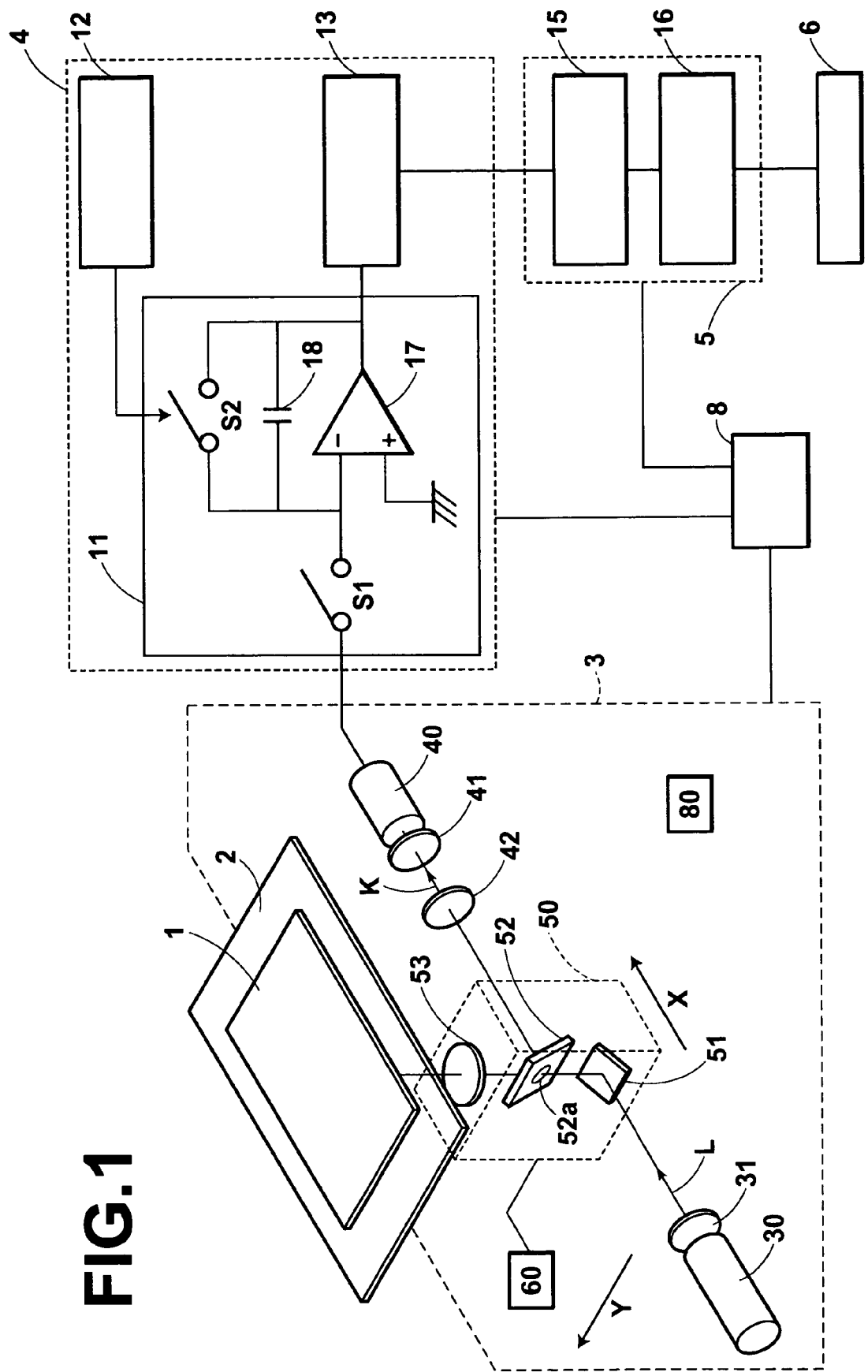
FIG. 1 is a diagram showing an optical information read system constructed in accordance with a preferred embodiment of the present invention.
Figure 2:
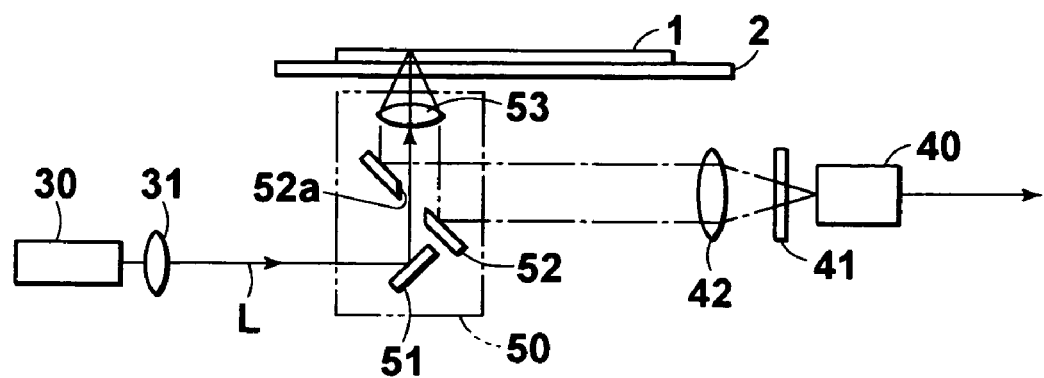
FIG. 2 is a side view of the light-intensity detection section shown in FIG. 1.

Referring to FIG. 1, there is shown an optical information read system constructed in accordance with a preferred embodiment of the present invention. The optical information read system includes six major components: (1) a storable phosphor sheet 1, which is a scan sheet, mounted on a transparent sheet mounting plate 2; (2) a light-intensity detection section 3 for detecting a light intensity by irradiating excitation light to the storable phosphor sheet 1 and receiving light that is emitted from the storable phosphor sheet 1; (3) a light-intensity pixel data generation section 4; (4) an image generation section 5 for generating light-intensity image data; (5) a display section 6 for displaying the generated light-intensity image data as a visible image; and (6) a control section 8 for controlling operations of the light-intensity detection section 3, light-intensity pixel data generation section 4, and image generation section 5.

The light-intensity detection section 3 comprises: (1) a laser light source 30 for emitting laser light L, that is, excitation light; (2) a collimator lens 31 for making the laser light L emitted from the laser light source 30 parallel; (3) a photomultiplier tube (hereinafter referred to as PMT) 40 as light-intensity detection means for photoelectrically detecting photostimulated luminescence (PSL) K that is emitted from the storable phosphor sheet 1 when struck by the laser light L; (4) an optical head 50 for irradiating the laser light L to the storable phosphor sheet 1 mounted on the sheet mounting plate 2, and guiding the photostimulated luminescence K to the PMT 40; (5) a laser light cut filter 41 disposed between the optical head 50 and the PMT 40; (6) a condenser lens 42 for collecting the photostimulated luminescence K emitted from the optical head 50, disposed between the optical head 50 and the PMT 40; (7) horizontal scanning means 60 for moving the optical head 50 at uniform speed in a horizontal scanning direction X; and (8) vertical scanning means 80 for moving the laser light source 30, lens 31, optical head 50, laser light cut filter 41, condenser lens 42, and PMT 40 as one body in a vertical scanning direction Y substantially perpendicular to the horizontal scanning direction X.

The light source 30 is arranged so the laser light L is emitted along the direction X. Similarly, the PMT 40 is arranged to detect the photostimulated luminescence K incident along the direction X.

The optical head 50 comprises (1) a plane mirror 51 for reflecting a collimated beam of laser light L in an upward direction perpendicular to the storable phosphor sheet 1; (2) a holed mirror 52, which has a small hole 52 formed to the degree that the reflected laser light L can pass through it, for reflecting the greater part of the photostimulated luminescence K emitted down from the storable phosphor sheet 1, in the direction X; and (3) an objective lens 53 for making the photostimulated luminescence K emitted from the top surface of the storable phosphor sheet 1 a nearly parallel beam. The plane mirror 51, holed mirror 52, and objective lens 53 are formed as one body.

To prevent the laser light L from entering the PMT 40 when part of the laser light L, scattered and reflected at the storable phosphor sheet 1 and sheet mounting plate 2, travels in the direction of the PMT 40 along with the photostimulated luminescence K, the laser light cut filter 41 is a band filter that transmits the photostimulated luminescence K and substantially attenuates the laser light L.

The vertical scanning means 80 conveys the storable phosphor sheet 1 at intervals of 50 μm in the vertical scanning direction Y. That is, the spacing in the vertical scanning direction Y between lines is 50 μm.

The light-intensity pixel data generation section 4 is equipped with an integrating amplifier 11 for sampling and quantizing analog signals output from the PMT 40, at predetermined sampling cycles; a clock circuit 12 for outputting a sampling clock signal to the integrating amplifier 11; and an A/D converter 13 for converting the analog light-intensity pixel data output from the integrating amplifier 11, to digital data.

Figure 3A:
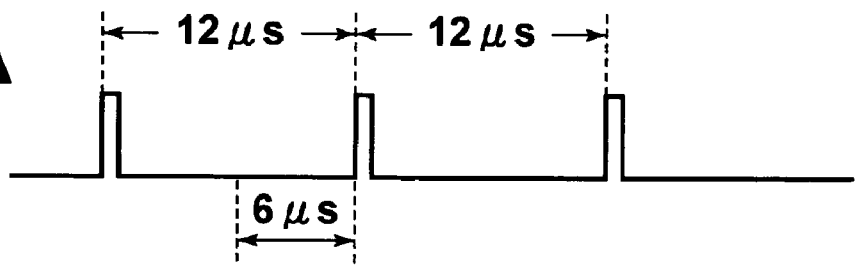
FIG. 3, which includes 3A and 3B, is a diagram showing the timing at which a sampling clock signal is output.
Figure 3B:
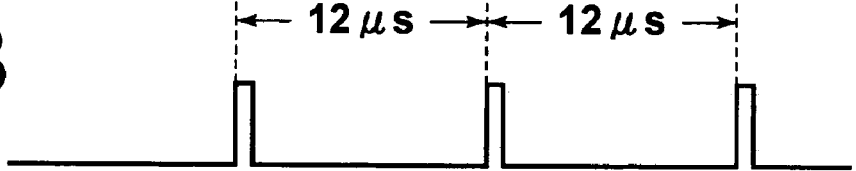

The integrating amplifier 11 comprises a first switch S1, an operational amplifier 17, a capacitor 18, and a second switch S2. If a sampling clock signal is input from the clock circuit 12, the second switch S2 is opened and closed. During the time the second switch S2 is open, a voltage value integrated by the integrating amplifier 11 is output. Note that the integrating time of the integrating amplifier 11 is 8 μs. The clock circuit 12 comprises an encoder clock, which outputs a sampling clock signal at cycles of 12 μs. In scanning odd-numbered horizontal scan lines, an A-phase close signal is output as shown in FIG. 3A. In scanning even-numbered horizontal scan lines, a B-phase close signal is output as shown in FIG. 3B. The A-phase close signal and B-phase close signal output from the encoder clock are shifted in output timing by one-half of the signal cycle.

The image generation section 5 is equipped with light-intensity image data acquisition section 15 for calculating interpolated light-intensity pixel data from the A/D-converted light-intensity pixel data, and generating light-intensity image data from the light-intensity pixel data and the interpolated light-intensity pixel data; and an image processing section 16 for performing desired image processing, such as an edge enhancement process, etc., on the light-intensity image data.

Note that the light-intensity detection section 3, light-intensity pixel data generation section 4, and light-intensity image data acquisition section 15 constitute the light-intensity image data generation means of the present invention.

Now, operation of the optical information read system of the preferred embodiment will be described with reference to the case where the storable phosphor sheet 1 is mounted on the top surface of the sheet mounting plate 2.

Initially, the horizontal scanning section 60 makes the optical head 50 move at uniform speed in the horizontal scanning direction X. During the time the optical head is moving, laser light L is being emitted from the laser light source 30 in a direction along the direction X. This laser light L is made a parallel beam by the lens 31 and enters the optical head 50. The laser light L incident on the plane mirror 51 is reflected upward and passes through the small hole 52a of the mirror 52. The laser light L is passed through the object lens 53 and irradiated onto a very small region on the top surface of the storable phosphor sheet 1.

If the laser light L is thus irradiated onto the storable phosphor sheet 1, the phosphor layer of the storable phosphor sheet 1 emits photostimulated luminescence K according to the radiation image information stored in the phosphor layer. The photostimulated luminescence K travels along the same optical path as the laser light L in the opposite direction and reaches the mirror 52 that has the small hole 52a. Since the photostimulated luminescence K is greater in diameter than the laser light L, part of the photostimulated luminescence K passes through the small hole 52a of the mirror 52, but the greater part is reflected toward the direction of the PMT 40 by the mirror 52. The photostimulated luminescence K is collected by the condenser lens 42 and strikes the PMT 40. Then, the photostimulated luminescence K is photoelectrically converted to an analog signal and output to the light-intensity pixel data generation section 4.

Note that part of the laser light L irradiated onto the storable phosphor sheet 1 is scattered and reflected at the storable phosphor sheet 1 and sheet mounting plate 2 and travels along the direction of the PMT 40 along with the photostimulated luminescence K. However, the scattered laser light L is attenuated by the laser cut light cut filter 41 disposed between the lens 52 and the PMT 40.

During the aforementioned operation, the optical head 50 is being moved at uniform speed in the horizontal scanning direction X by the horizontal scanning means 60. When the sampling interval is 12 μs, the moving speed of the optical head 50 is set so that light-intensity pixel data is read out from the storable phosphor sheet 1 at sampling intervals of 100 μm.

If the horizontal scanning in the direction X with respect to the storable phosphor sheet 1 is finished, the vertical scanning means 80 moves the laser light source 30, lens 31, optical head 50, condenser lens 42, laser light cut filter 41, and PMT 40 integrally in the vertical scanning direction Y by 50 μm. Then, the aforementioned horizontal scanning is repeated.

By combining the aforementioned horizontal scanning and vertical scanning together, laser light L is irradiated over the entire surface of the storable phosphor sheet 1, and an image signal corresponding to each location on the storable phosphor sheet 1 is acquired.

The first switch S1 of the light-intensity pixel data generation section 4 is closed at the start of the scanning of each horizontal scan line and is opened at the end of the scanning of that horizontal scan line.

The analog light-intensity pixel data output from the integrating amplifier 11 is converted to digital light-intensity pixel data by the A/D converter 13 and is stored in the image memory (not shown) of the light-intensity image data acquisition section 15 of the image processing section 5.

Figure 4A:
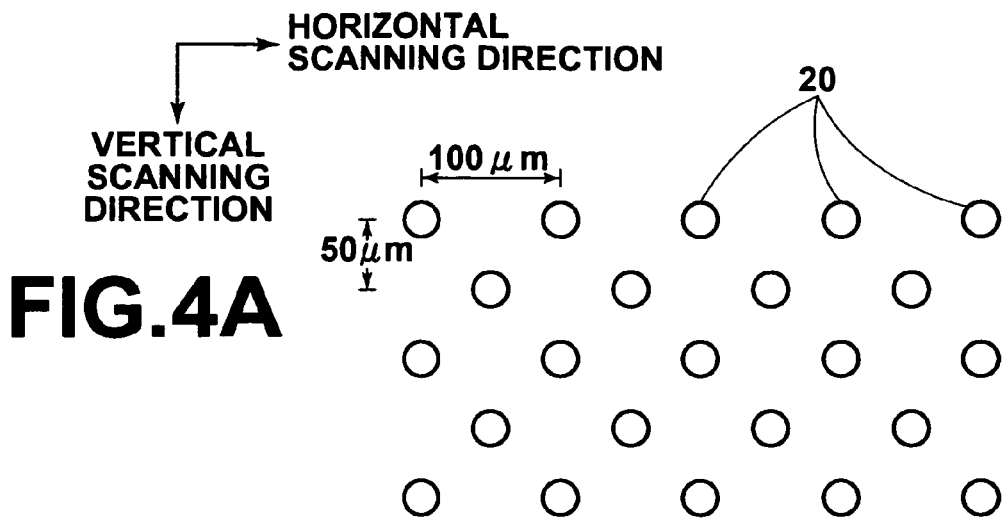
FIG. 4, which includes 4A and 4B, is a diagram used to explain light-intensity pixel data and interpolated light-intensity pixel data.

When scanning odd-numbered scan lines, a sampling clock signal is input to the second switch S2 of the integrating amplifier 11 at sampling timing such as that shown in FIG. 3A. When scanning even-numbered scan lines, a sampling clock signal is input to the second switch S2 of the integrating amplifier 11 at sampling timing such as that shown in FIG. 3B. Therefore, the light-intensity pixel data acquired by scanning odd-number scan lines, and the light-intensity pixel data acquired by scanning even-number scan lines, become light-intensity pixel data 20 alternately read out in the horizontal scanning direction, as shown in FIG. 4A.

Figure 4B:
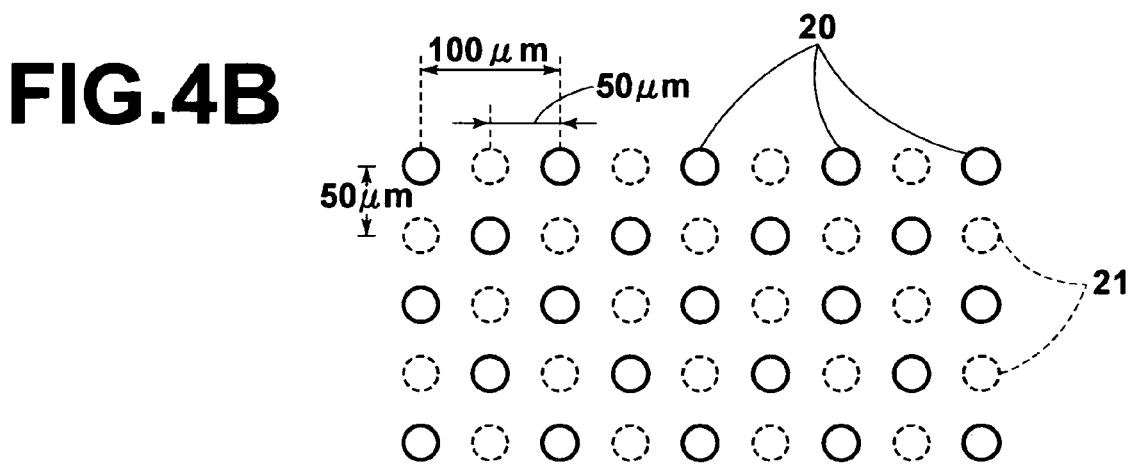

The light-intensity image data acquisition section 15 calculates interpolated light-intensity pixel data 21 shown by dotted lines in FIG. 4B. The interpolated light-intensity pixel data 21 can be calculated by various methods. For instance, each of the interpolated light-intensity pixel data can be obtained by calculating the average value of four light-intensity pixel data on the vertical and horizontal sides of each of the interpolated light-intensity pixel data 21.

The light-intensity image data acquisition section 15 generates light-intensity image data by interpolating the interpolated light-intensity pixel data into the light-intensity pixel data, and outputs it to the image processing section 16. The sampling interval in the horizontal scanning direction is 100 μm and the sampling interval in the vertical scanning direction is 50 μm. Therefore, the data spacing in the light-intensity image data acquired by interpolating the interpolated light-intensity pixel data into the light-intensity pixel data is 50 μm in the horizontal scanning direction and also 50 μm in the vertical scanning direction.

The image processing section 16 performs desired image processing, such as an edge enhancement process, etc., on the light-intensity image data and outputs the data to the display section 16. The display section 16 displays the light-intensity image data as a visible image. When outputting to an external device, etc., the image processing section 16 performs a thinning-out operation on the light-intensity image data to reduce the amount of the data, and may output the thinned-out data.

As has been described above, the preferred embodiment acquires checkered light-intensity pixel data by shifting the sampling timing of even-numbered horizontal scan lines and the sampling timing of odd-numbered horizontal scan lines by one-half of the sampling cycle. Then, the interpolated light-intensity pixel data for the checkered light-intensity pixel data are calculated from the light-intensity pixel data arranged around the interpolated light-intensity pixel data. And based on the light-intensity pixel data and the interpolated light-intensity pixel data, light-intensity image data is generated. Therefore, the data spacing in the light-intensity image data can be shortened without increasing the pixel density of the light-intensity pixel data acquired from the storable phosphor sheet 1. That is, resolution can be practically doubled and the visibility of a visible image displayed can be enhanced.

In addition, checkered light-intensity pixel data can be easily obtained by only shifting the sampling timing of even-numbered horizontal scan lines from the sampling timing of odd-numbered horizontal scan lines by one-half of the sampling cycle, without considerably changing the construction of existing optical information read systems.

The sampling interval in the horizontal scanning direction is twice the spacing in the vertical scanning direction between the scan lines. For this reason, if the interpolated light-intensity pixel data is interpolated into the light-intensity pixel data, the data spacing in the horizontal scanning direction becomes equal to the data spacing in the vertical scanning direction. Therefore, visibility in making the light-intensity image data visible can be enhanced.

In the optical information read system of the preferred embodiment, it has been described and illustrated that the horizontal scanning means 60 moves the optical head 50 in the horizontal scanning direction and the vertical scanning means 80 moves the laser light source 30, lens 31, optical head 50, condenser lens 42, laser light cut filter 41, and PMT 40 integrally in the vertical scanning direction. However, the storable phosphor sheet 1 may be moved in the horizontal scanning and vertical scanning directions. In addition, the PMT 40 may be moved with respect to the storable phosphor sheet 1 by moving the optical head 50 and lens system, without moving the laser light source 30 or PMT 40.

Figure 5:
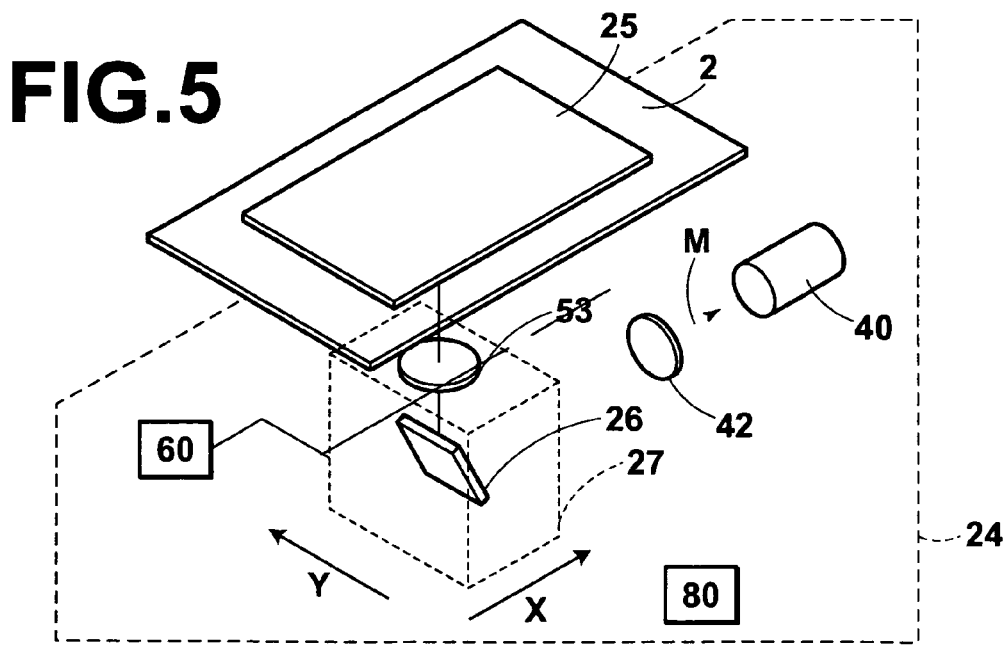
FIG. 5 is a perspective view showing another light-intensity detection section.

As a variation of the preferred embodiment, an optical information read system is equipped with a light-intensity detection section 24 instead of the light-intensity detection section 3, as shown in FIG. 5. This system acquires light-intensity image data that represents the distribution of inspection substances labeled with a chemical luminescence labeling body, by bringing a chemical luminescent substrate into contact with a scan sheet 25 in which the inspection substances labeled with the chemical luminescence labeling body are distributed, and photo electrically reading out a light intensity of chemical luminescence M emitted from the chemical luminescent substrate. Since excitation light is unnecessary, the aforementioned laser light source and laser light cut filter are omitted and an optical head 27 with an ordinary mirror 26 instead of the holed mirror 52 is employed.

What is claimed is:

1. An optical information read method of scanning an entire surface of a scanned body by repeatedly moving light-intensity detection means, which detects a light intensity by receiving light that is emitted from said scanned body, relatively with respect to said scanned body in a horizontal scanning direction and in a vertical scanning direction nearly perpendicular to said horizontal scanning direction, and acquiring light-intensity image data of the light emitted from said scanned body, based on an output signal from said light-intensity detection means, said optical information read method further comprising the step of:

acquiring checkered light-intensity pixel data from said scanned body, calculating interpolated light-intensity pixel data from said light-intensity pixel data arranged around said interpolated light-intensity pixel data, and generating said light-intensity image data, based on said light-intensity pixel data and said interpolated light-intensity pixel data.

2. An optical information read system which comprises light-intensity detection means for detecting a light intensity by receiving light that is emitted from a scanned body, and which scans an entire surface of said scanned body by repeatedly moving said light-intensity detection means relatively with respect to said scanned body in a horizontal scanning direction and in a vertical scanning direction nearly perpendicular to said horizontal scanning direction and acquires light-intensity image data of the light emitted from said scanned body, based on an output signal from said light-intensity detection means, said optical information read system further comprising:

light-intensity image data generation means for acquiring checkered light-intensity pixel data from said scanned body, calculating interpolated light-intensity pixel data from said light-intensity pixel data arranged around said interpolated light-intensity pixel data, and generating said light-intensity image data, based on said light-intensity pixel data and said interpolated light-intensity pixel data.

3. The optical information read system as set forth in claim 2, wherein said light-intensity image data generation means acquires said light-intensity pixel data by quantizing the output signal of said light-intensity detection means at predetermined sampling cycles; and timing at which even-numbered horizontal scan lines are sampled is shifted from timing at which odd-numbered horizontal scan lines are sampled, by one-half of said sampling cycle.

4. The optical information read system as set forth in claim 3, wherein a sampling interval in said horizontal scanning direction is twice the spacing in the vertical scanning direction between said scan lines.

5. The optical information read system as set forth in claim 2, wherein the light emitted from said scanned body is light that is emitted from said scanned body when scanned with excitation light.

6. The optical information read system as set forth in claim 3, wherein the light emitted from said scanned body is light that is emitted from said scanned body when scanned with excitation light.

7. The optical information read system as set forth in claim 4, wherein the light emitted from said scanned body is light that is emitted from said scanned body when scanned with excitation light.

8. The optical information read method of claim 1, wherein calculating interpolated light-intensity pixel data from said light-intensity pixel data arranged around said interpolated light-intensity pixel data is performed by directly using averages of said light-intensity pixel data arranged around said interpolated light-intensity pixel data.

9. The optical information read method of claim 1, wherein calculating interpolated light-intensity pixel data from said light-intensity pixel data arranged around said interpolated light-intensity pixel data is performed by using the average value of four light-intensity pixel data on the vertical and horizontal sides of each of the interpolated light-intensity pixel data.

10. The optical information read method of claim 1, wherein calculating interpolated light-intensity pixel data from said light-intensity pixel data arranged around said interpolated light-intensity pixel data is performed without comparing values of said light-intensity pixel data arranged around said interpolated light-intensity pixel data.

11. The optical information read system as set forth in claim 2, wherein calculating interpolated light-intensity pixel data from said light-intensity pixel data arranged around said interpolated light-intensity pixel data is performed by directly using averages of said light-intensity pixel data arranged around said interpolated light-intensity pixel data.

12. The optical information read system as set forth in claim 2, wherein calculating interpolated light-intensity pixel data from said light-intensity pixel data arranged around said interpolated light-intensity pixel data is performed by using the average value of four light-intensity pixel data on the vertical and horizontal sides of each of the interpolated light-intensity pixel data.

13. The optical information read system as set forth in claim 2, wherein calculating interpolated light-intensity pixel data from said light-intensity pixel data arranged around said interpolated light-intensity pixel data is performed without comparing values of said light-intensity pixel data arranged around said interpolated light-intensity pixel data.

14. The optical information read method of claim 1, wherein the acquiring checkered light-intensity pixel data is obtained from scanning the entire surface of said scanned body.

15. The optical information read method of claim 14, wherein the entire surface of said scanned body includes light emissions from the entire surface read by said light-intensity detection means.

* * * * *